United States Patent [19]
Müller

[11] Patent Number: 6,139,503
[45] Date of Patent: Oct. 31, 2000

[54] INVASIVE BLOOD PRESSURE MEASUREMENT DEVICE

[75] Inventor: Daniel Müller, Kirchseeon, Germany

[73] Assignee: PVB Medizintechnik GmbH & Co. KG, Kirchseeon, Germany

[21] Appl. No.: 09/320,490

[22] Filed: May 26, 1999

[51] Int. Cl.$^7$ ...................................................... A61B 5/02
[52] U.S. Cl. ........................... 600/486; 600/488; 600/500
[58] Field of Search .................................... 600/479, 486, 600/488, 500; 73/708, 706, 715

[56] References Cited

U.S. PATENT DOCUMENTS

| | | | |
|---|---|---|---|
| 4,603,574 | 8/1986 | Norman | 73/4 |
| 5,540,100 | 7/1996 | von Berg | 73/756 |
| 5,622,179 | 4/1997 | Pfandal et al. | 128/897 |
| 5,769,083 | 6/1998 | MacEachern | 600/486 |

FOREIGN PATENT DOCUMENTS

| | | | |
|---|---|---|---|
| 0 124 308 | 4/1984 | European Pat. Off. | A61B 5/00 |
| 0 366 651 | 12/1987 | European Pat. Off. | A61B 5/02 |
| 0 672 381 | 2/1995 | European Pat. Off. | A61B 5/215 |
| 43 17 985 | 5/1993 | Germany | A61B 19/00 |
| 44 00 941 | 1/1994 | Germany | G01L 9/00 |
| 295 06 589 | 4/1995 | Germany | A61B 5/215 |
| 97/39679 | 10/1997 | WIPO | A61B 5/02 |

*Primary Examiner*—Cary O'Connor
*Assistant Examiner*—Ryan Carter
*Attorney, Agent, or Firm*—Senniger, Powers, Leavitt & Roedel

[57] ABSTRACT

A pressure transducer arrangement featuring a holding element for a number of pressure transducers. For each pressure transducer a group of electronic counter-contacts is provided on the holding element that are in contact with the contacts of the pressure transducer while it is attached to the holding element. All counter-contacts are connected to one common signal transfer device.

17 Claims, 9 Drawing Sheets

INVASIVE BLOOD PRESSURE MEASUREMENT DEVICE

BACKGROUND OF THE INVENTION

The invention pertains to a pressure transducer arrangement for the measuring of fluid pressure, particularly for invasive blood pressure measuring.

EP 0,124,308 A2 shows a pressure transducer arrangement with three components, namely a single use pressure transducer, a holding element and a connecting cable to a monitor. The actual pressure measuring element, which is connected to a chamber that can be charged with the fluid pressure to be measured, is encapsulated in a housing of the pressure transducer. The pressure measuring element is fitted with electronic connectors that can be inserted into matching connectors of the holding element. The holding element also has a housing that is shaped appropriately to hold the housing of the pressure transducer. The matching contacts on the holding element housing are connected to the cable. After use, the pressure transducer housing can be manually removed from the holding element and can be replaced with a new pressure transducer housing.

A similar pressure transducer arrangement is known from DE 4,400,941 that also consists of three components, namely a pressure transducer, a cable with a connector and a holding element to hold the pressure transducer and the connector.

The pressure transducer has a housing with two chambers, a fluid channel and two fluid connections. One of the connections is connected to the vascular system of a patient and the other one to an infusion bottle, which permits an infusion of e.g. physiological saline solution for the prevention of blood coagulation in the conducting system. A measuring instrument is positioned in the housing chamber, which is located between the two connections, and the instrument is fixed on a substrate and is pressure-connected to the fluid channel. Further, strip conductors are provided on the substrate that are connected to the pressure measuring element and with other electronic components of a measuring circuit. The substrate and the strip conductors are extended into the interior of the second housing chamber. There, the ends of the strip conductors form connectors that can be accessed through an opening in the housing wall. The plug is configured to match the housing opening and the contacts, and contains matching contacts for the contacts that are connected to the cable wires. On its top, the holding element contains holding rails into which the pressure transducer can be inserted.

When measuring blood pressure, the pressure transducer is attached to the holding element and the plug is inserted in such a way that the contacts touch the matching contacts. A blood pressure that is present in the pressure transducer is measured by the pressure measuring element and transformed into an electronic signal that is transferred to a monitor through the cable. Frequently, during surgery or with patients in intensive care, several pressures have to be measured simultaneously, which requires the use of several pressure transducers. Accordingly, the said holding elements are configured in a modular fashion so that several holding elements, each with one pressure transducer, can be positioned alongside each other. Separate cables lead from these holding elements to the monitor, one for each pressure transducer. The multitude of cables and hoses renders the measuring arrangement rather confusing and creates the danger that mix-ups may occur when changing the pressure transducers and that nursing personnel may trip over the cables.

Further, the pressure transducers are regularly exchanged for each patient, disposed of and replaced with new ones, while the holding elements and cables are reused (compare DE 4,317,985 A1). The hoses must be disconnected and connected to the new pressure transducers when changing the pressure transducers. In this process, blood or infusion fluid may be spilled on the new pressure transducer or on the holding elements.

Pressure transducers of the type described here are customarily equipped with a Wheatstone bridge, with one branch of the bridge containing a pressure-sensitive resistor. Normally, during function testing, this branch is jumped with a defined resistor. The monitor will usually display a test value of 100 mm/Hg. Switching in this resistor is accomplished by means of a key, usually located on the monitor, on the pressure transducer itself (DE 4,400,941) or together with a shunt resistor on the cable (EP 0,366,651 C2 and U.S. Pat. No. 4,603,574). In the event that the key is located on the monitor or on the cable, the key is reusable even if the pressure transducer is discarded after use.

A pressure transducer arrangement is known from DE 29,506,589 U1 that features several so-called "pressure domes" that are each connected to the patient and to the infusion bottle and are disposed of after one use. The pressure domes are mounted on reusable holding elements that are positioned alongside each other in a modular fashion. Each holding element features a reusable pressure measuring element with a pressure transfer membrane that interacts with a pressure transfer membrane on the outside of the corresponding pressure dome. In this case, too, a cable goes out from each pressure measuring element, which leads to the aforementioned problems.

SUMMARY OF THE INVENTION

It is the objective of the invention to improve the arrangement of pressure transducers of the mentioned type in such a manner as to make their structure compact and simple, their operation reliable and to allow their quick and easy connection with a monitor or other electronic equipment.

This objective is solved through the characteristics of claims 1 and 12. Useful embodiments and refinements of the invention can be found in the sub-claims.

The primary principle of the invention is to configure the holding element so that several pressure transducers can be attached to it, so that there is a group of matching contacts on the holding element for each pressure transducer, and so that all of the matching contacts are connected to a single signal transfer device. According to another variant of the invention, the pressure transducers that transform the pressure to be measured into an electronic signal are located in the interior of the holding element and several single use pressure domes are attached to the holding element. On the holding element, one transfer membrane is provided for each pressure dome that can be brought into contact with a counter membrane on the pressure dome. In this case, as well, the signals of the individual measuring channels are transferred from the holding element to a monitor, recording device or the like via a single signal transfer device.

Preferentially, the signal transfer device is either a cable or a wireless transfer line such as e.g. infrared, radio or ultrasound. In the first variant of the invention with single use pressure transducers the preferential configuration of the invention provides for contacts or matching contacts on the external surface of the pressure transducer and on the corresponding external surface of the holding element that are put into contact with each other when the pressure transducer is attached to the holding device.

In a refinement of the invention, essential parts of the pressure transducer such as e.g. various electronic resistors, the already mentioned test key, etc., are located inside the holding element so that these components are reusable and so that the single use part contains fewer components than before, which will reduce cost and waste.

Preferentially, the signal transfer device should be manually detachable from the holding element, particularly if it is a cable. In this fashion, the holding element and/or the cable can be individually exchanged if required. Practical work has shown that the cables are stressed severely and have to be exchanged frequently. According to a refinement of this concept, the cable connectors on the monitor side are also individually exchangeable. In a practical situation, these connectors that connect to the monitor are subject to relatively little wear and they are also extremely expensive and according to this variant of the invention they would not have to be exchanged any more.

Another advantage of the invention resides in the fact that the holding element also assumes the function of the otherwise normal holding plate (compare DE 4,317,985 A1). In EP 0,124,308, as well, the holding element that is used is S also attached to a holding plate, which is itself usually attached to an infusion stand. Thus, the state of the art required a two-step operation in which first the pressure transducer was positioned on the holding element and then this unit was fastened to the holding plate. The invention consolidates the establishment of an electronic or pressure transferring connection between the pressure-measuring element or the pressure dome and the holding element into one single operational step. Another advantage resides in the fact that only a signal transfer device and a single cable lead to the monitor. Erroneous exchanges or misidentifications of the cables are thus eliminated.

Additionally, there is no longer a need to route an individual insulated conductor of the cable to each counter contact when using a cable. Counter contacts for voltage and ground can each be routed through a single insulated conductor of the cable, while corresponding wiring or a printed-circuit board are simply located within the holding element. In this fashion, the cable needs fewer insulated conductors and accordingly can be thinner, which reduces costs as well. Obviously, these advantages also apply to the pressure transducer arrangement with the single use pressure domes.

A problem that might result from the pressure transducer arrangement according to the invention could reside in the fact that when hoses are detached, fluids such as e.g. physiological saline solution can get on the holding element and in particular on the contacts or on the new pressure transducer and its contacts. Physiological saline solution is a relatively good electronic conductor and therefore a fluid film developing between neighboring contacts could cause a shunt resistance to develop and the resulting measurement to be in error. To solve this consequential problem, the invention suggests to locate and/or configure the contacts and counter contacts in such a fashion that a fluid film that might bridge the contacts cannot develop during practical use or would be partially or totally disrupted or wiped away when establishing the electronic contact. For this purpose, e.g. sealing elements, which would displace a fluid film, could be positioned around the contacts and/or counter contacts. Likewise, provisions could be made for the contacts and counter contacts to penetrate the elastic seals only when mechanically connecting the pressure transducer to the holding element and that until then they would be protected against fluids. Also, many options exist for the configuration of the contacts and counter contacts such as e.g. touch contacts, clamping contacts, plug-socket combinations, spring-loaded contact pins, insulation displacement contacts or other electronic connecting devices.

Finally, according to a refinement of the invention, the aforementioned test key and its electronic contacts are incorporated on or in the holding element.

BRIEF DESCRIPTION OF THE FIGURES

Below the invention is explained in detail by means of embodiment examples in connection with the drawings. Shown are.

DETAILED DESCRIPTION OF THE INVENTION

Figure 1:
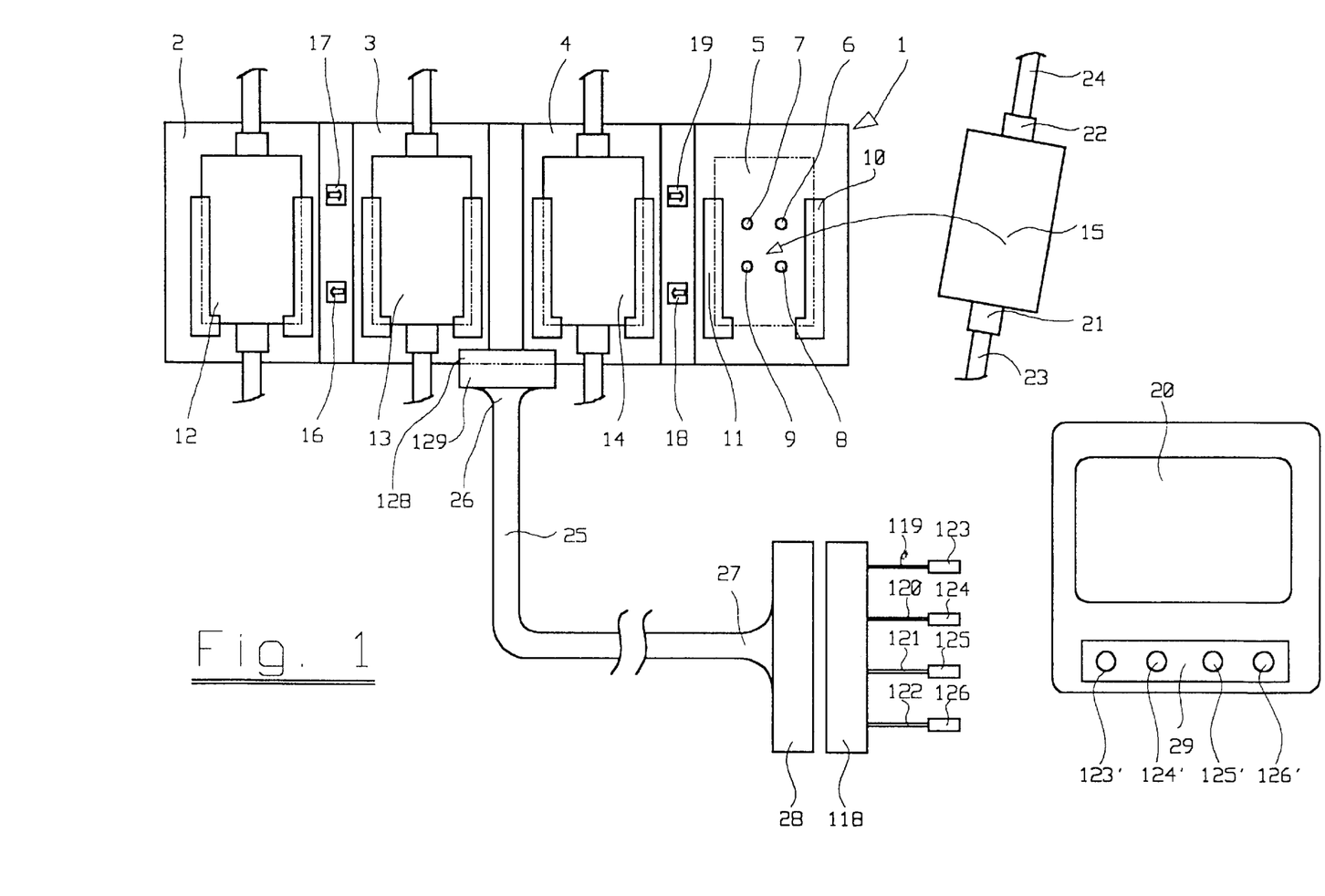
FIG. 1, a schematic description of the pressure transducer arrangement according to the invention with a holding element for attachment and connection of several pressure transducers.

FIG. 1 shows a diagram of a pressure transducer arrangement with a holding element 1 that has four pressure measuring positions 2, 3, 4 and 5. At each of the pressure measuring positions 2, 3, 4, and 5, four holding plate contacts 6, 7, 8 and 9 are provided that are here positioned directly on the shown external surface of the front side of the holding element 1. Furthermore, two engagement elements 10 and 11 are each provided for the detachable attachment of pressure transducers 12, 13, 14 and 15 at the pressure measuring positions 2, 3, 4, and 5. In FIG. 1 the pressure transducer 12, 13 and 14 are attached to the corresponding pressure measuring positions 2, 3, and 4 of the holding element 1, while pressure transducer 15 has been removed.

Each one of the pressure transducers 12, 13, 14 and 15 shown in the diagram has a first fluid connection 21 and a second connection 22, with which hoses 23 and 24, respectively, are connected. For example, connection 21 is connected to a patient blood vessel by means of hose 23, while the other hose 24 can be connected to an infusion bottle.

Inside each pressure transducers 12, 13, 14 and 15, one pressure measuring element is contained (shown in FIG. 3) that is electrically connected to holding plate contacts 6, 7, 8, and 9, which correspond with pressure transducers 12, 13, 14 and 15, respectively, that are attached to the holding element 1.

For each pressure transducer 12, 13, 14 and 15, a corresponding test key 16, 17, 18, and 19 is provided on the holding element 1. Test keys 16, 17, 18 and 19 permit function testing of the corresponding pressure transducers 12, 13, 14 and 15, respectively. For this purpose electronic contacts of the test keys 16, 17, 18 and 19 are connected inside the holding element 1 to the corresponding holding plate contacts, and through activation of the test keys, a resistor of a branch of the bridge in the corresponding pressure transducer is modified in a defined way. Alternatively, a single test key can be provided for all pressure transducers that would simultaneously, and in a defined way, modify the pressure transducers of all the branches of the bridge.

A cable 25 is attached to holding element 1, and the insulated conductors of the cable (FIG. 2) are each connected electrically to a corresponding holding plate contact, while a first end 26 of cable 25 is connected to holding element 1. At the free end 27 of cable 25, a connector part 28 is provided. Connector part 28 can be so configured that it can be plugged directly into a socket part 29 of a monitor 20. Also, at the end of the cable that is oriented toward the holding element 26, a connector 129 can be attached to corresponding counter contacts 128 on or in holding element 1. Alternatively, the end 26 of the cable on the holding plate side also can be soldered to a printed circuit (FIG. 2) in the holding element 1.

In the variant shown in FIG. 1, the free end 27 of cable 25 is equipped with a connector part 28 that can be connected to matching connector 118, single short cables 119, 120, 121 and 122 extend out of each measuring channel and a monitor connector 123, 124, 125 and 126 is attached to each end of the cables, respectively, and these connectors can be plugged into corresponding sockets 123', 124', 125' and 126', respectively, on the monitor 20. Thus, the cable 25 can be exchanged with connectors 129 and 28, without having to exchange the expensive monitor connectors 123–126.

Figure 2:
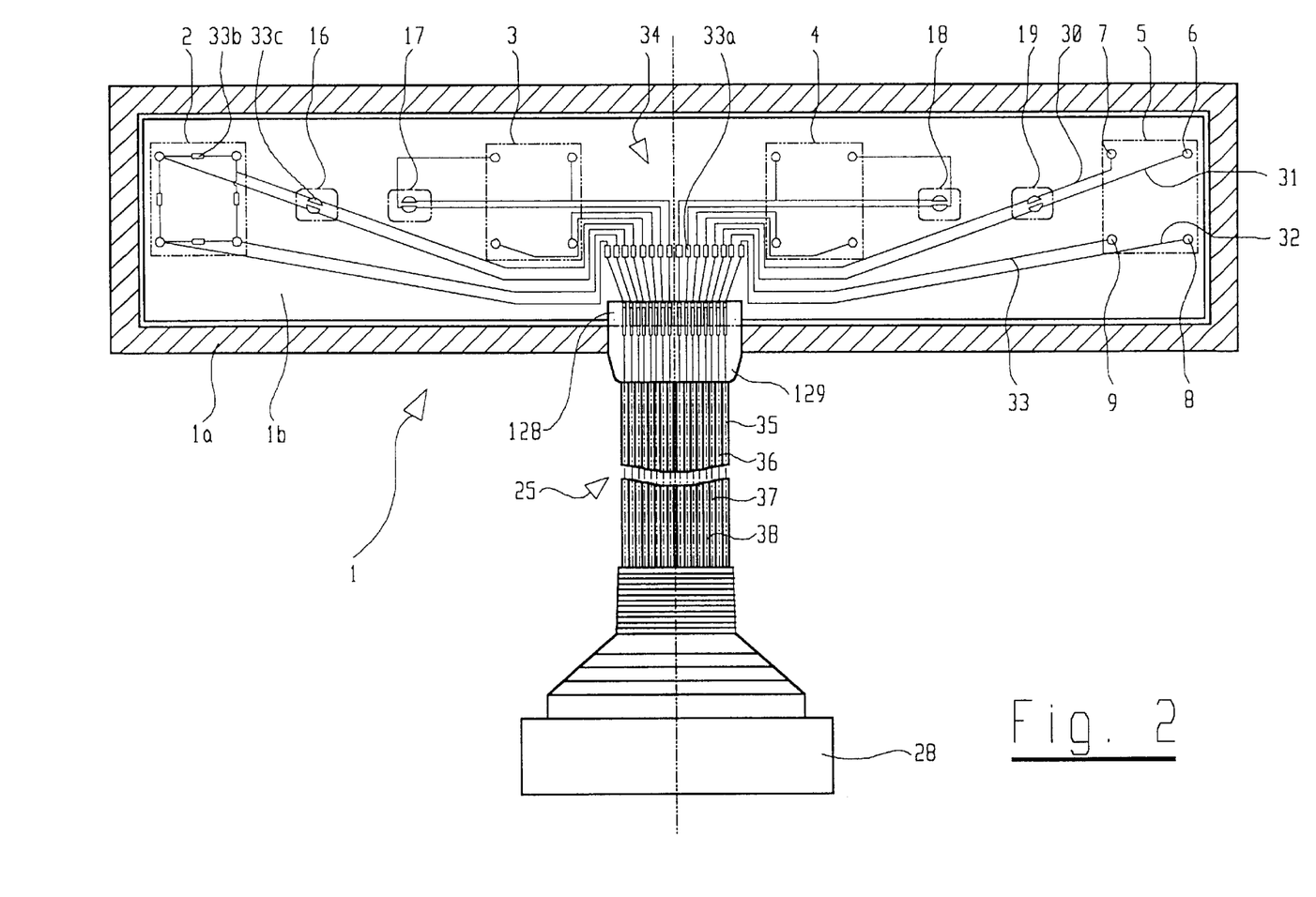
FIG. 2, a view of an opened holding element showing the wiring of the counter contacts.

FIG. 2 shows a front view in partial cross section of an opened holding element 1 with a housing 1a into which a printed-circuit board 1b is inserted showing the electrical connections of the holding plate contacts 6, 7, 8 and 9 to cable 25. In accordance with holding element 1 shown in FIG. 1, four pressure measuring locations 2, 3, 4 and 5 are provided each showing four holding plate contacts that are marked as an example at attachment location 5 with the reference marks 6, 7, 8 and 9. Each of the holding plate contacts 6, 7, 8 and 9 is connected to a cable 30, 31, 32 and 33, respectively, routed in a middle area 34 of holding element 1 and there electrically connected to the corresponding strands 35, 36, 37 and 38, respectively, of cable 25. On the printed-circuit board 1b additional various resistors 33a are printed that are here shown as protective resistors in each line and that can serve e.g. to compensate temperature errors and/or as voltage divider in order to arrange the actual measuring circuit in a symmetrical configuration in relation to the power source. Similarly at the individual measuring positions resistors 33b can be printed between the holding plate contacts 6, 7, 8 and 9 that form part of the bridge circuit and constitute balancing resistors respectively. Also, switch contact surfaces 33c are printed on the printed-circuit board 1b in the area of the test keys 16–19, each in electrical contact with the corresponding strip conductor, whereas the test key (not shown) that is located in a movable position in the housing cover (also not shown) bears an electrically conductive coating on the side that points toward the printed-circuit board 1b, which, when the key is depressed, makes contact with the two switch contact surfaces 33c and thereby connects the corresponding lines.

The two lines 30 and 31 serve, e.g., as supply lines for the corresponding pressure transducer 12 (FIG. 1) and the other lines 32 and 33 serve as data lines for the transmission of measuring signals from the pressure transducer 12 to connector 28 and to the monitor (20) connected to it.

A test key 16, 17, 18 and 19 is assigned to each of the pressure measuring positions 2, 3, 4, and 5, shown here only schematically. Activating test key 19 assigned to plug-in position 5 jumps the two lines 30 and 31, respectively, that are connected to contacts 6 and 7 which, provided the pressure transducer 12 installed at pressure-measuring position 5 functions correctly, will produce a predefined test signal that can be recorded at the monitor 20 (FIG. 1). In the event that a malfunction occurs at the pressure transducer 12 or at the electrical contacts 6, 7, 8 or 9, the test signal will be different from the predefined value when the test key 19 is activated.

In the configuration shown, cable 25 with the plug/socket connection 128, 129 is connected to the individual lines, such as 30–33. The socket element is attached to the printed-circuit board 1b and/or to the housing 1a. Alternatively, cable 25 can also be directly soldered to the individual lines of the printed-circuit board.

FIG. 2 illustrates that essential components, such as resistors 33a, 33b, and the switch contact surfaces 33c, including the pertinent test keys and various electronic lines, are positioned in the re-usable holding element 1 and no longer—as in state of the art equipment—in the one-way pressure transducer.

Figure 3:
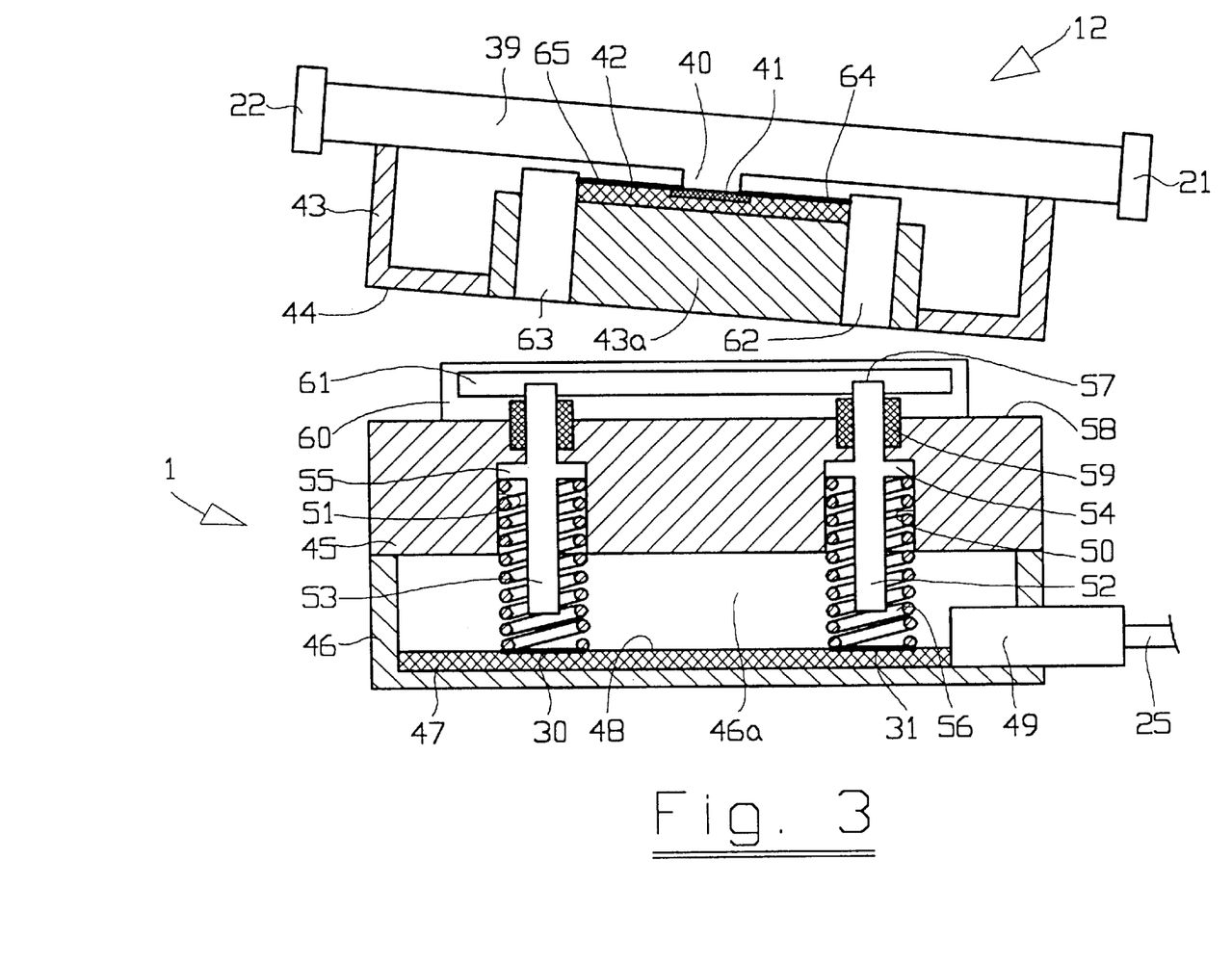
FIG. 3, an embodiment example of a pressure transducer arrangement with spring-loaded contact pins on the holding element.

FIG. 3 shows an embodiment example of a pressure transducer arrangement with the pressure transducer 12 disassembled from holding element 1. The two connections 21 and 22 are the end of a pressure measuring channel 39 that is part of a housing 43 of the pressure transducer 12. In its center part, pressure-measuring channel 39 displays a short blind channel 40 the end of which is here directly closed by a pressure measuring element 41. Alternatively, an intermediate medium can be applied to pressure-measuring element 41, e.g. a contact gel, so that a fluid contained in channel 39 would not directly wet the pressure-measuring element.

Pressure measuring element 41 is attached to a substrate 42 that is positioned inside the housing 43. Via connecting lines, of which here only lines 64 and 65 are seen, pressure-measuring element 41 is electrically connected to contact pins 62 and 63, respectively. Contact pins 62 and 63 and substrate 42 are attached to a locking piece 43a that is inserted into the housing 43, closing it at its exterior side 44. Alternatively to the embodiment example shown here in which the contact pins 62 and 63 end flush with the external surface of housing 43, the pins could also protrude above the external surface 44 or be recessed into the housing.

Holding element 1 features an upper housing part 45 and a lower housing part 46. Within a cavity 46a of the lower housing part 46 a printed-circuit board or substrate 47 is located that, at its bottom side 48, is equipped with printed traces, of which in the side view shown only the two printed traces 30 and 31 are visible. Printed traces 30 and 31 are connected to strands of cable 25 either by means of direct soldering or via a connecting piece 49 that could be, e.g., a socket with plug.

The upper housing part 45 is connected to the lower housing part 46 by means of, e.g., adhesive material, ultrasonic welding, form-fitting engagement, etc. Two recesses 50 and 51 are provided in the upper housing part 45 in which contact pins 52 and 53 are respectively located that have shoulders 54 and 55, respectively. Contact pin 52 is electrically connected via a spring 56 to printed trace 31 that is located on the upper side 48 of substrate 47, wherein one end of spring 56 presses directly against printed trace 31 while the other end of spring 56 presses against shoulder 54. Analogously, contact pin 53 is electrically connected to printed trace 30, which, in turn, is connected to cable 25. If the pressure transducer 12 has been removed, as is the case in FIG. 3, contact pins 52 and 53 will be pushed into their extreme positions by springs 56 with the shoulders 54 and 55 positioned at the "bottom" of the two recesses.

Contact pins 52 and 53 are shown in this embodiment example to be of sufficient length that their contact surfaces 57 extend beyond a surface 58 of the upper housing part 45. Within the surface 58 of the upper housing 45 an elastic sealing element 59 is attached that surrounds the upper stem of contact pin 52 sealing the holding element 1.

The upper housing 45 features at its upper surface 58 a fixture element 60 with an engagement element 61. When pressure transducer 12 is attached to holding element 1, contacts 62 and 52 and, respectively, 63 and 53 touch, by which action pressure-measuring element 41 is electrically connected to cable 25. By pushing down pressure transducer 12, contact pins 52 and 53 are pushed into the holding element 1 against the force of the springs until the housing 43 of pressure transducer 12 engages with fixture element 60 and 61, respectively. In this process, the elastic sealing elements 59 deform, laterally displacing any fluid that might have remained on top of upper surface 58 of the housing 1, thereby disrupting a possibly existing fluid film.

In addition it is possible to protect contacts 62 and 63 of the unused pressure transducer 12 against humidity or moisture by means of a protective coating or the like; the protection can be removed just before using pressure transducer 12 or it can be applied in such a way that it will be destroyed when it is attached to holding element 1, e.g., by contacts 52 and 53 piercing through the protective coating.

Figure 4:
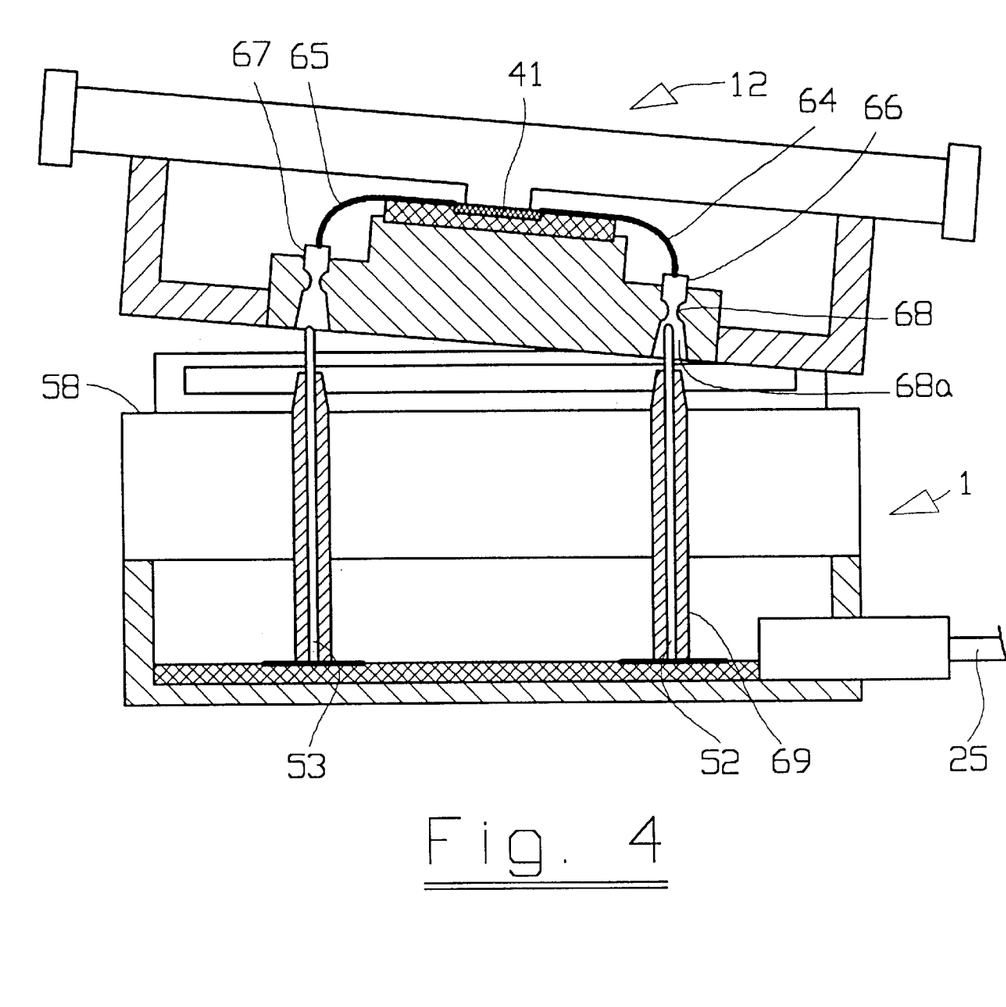
FIG. 4, an embodiment example with terminal and pin contacts.

FIG. 4 shows an embodiment example that is similar to the one in FIG. 3, whereas here terminal contacts 66 and 67 are provided in pressure transducer 12 that are connected to pressure measuring element 41 by means of lines 64 and 65. Terminal contacts 66 and 67 each feature a terminal buckle 68 and have a conical configuration in the insertion area 68a. The holding element 1 features contact pins 52 and 53 that are here firmly connected to holding part 1 and protrude from its upper surface 58. The contact pins 52 and 53 are enveloped by cylindrical sealing element 69 out of elastic material that extends a short distance above the upper side 58 of the housing, and in this area is shaped conically in accordance with the insertion areas 68a of the terminal contacts 66 and 67, respectively.

By attaching the pressure transducer 12 to the holding element 1, the contact pins 52 and 53 enter into terminal contacts 66 and 67, touching terminal buckle 68 and establishing an electronic connection between the pressure measuring element 41 and cable 25. In this process, the sealing elements 69 deform slightly, sealing holding element 1 and, if necessary, removing any fluid that may have been present on the contact pins 53, 54.

Figure 5A:
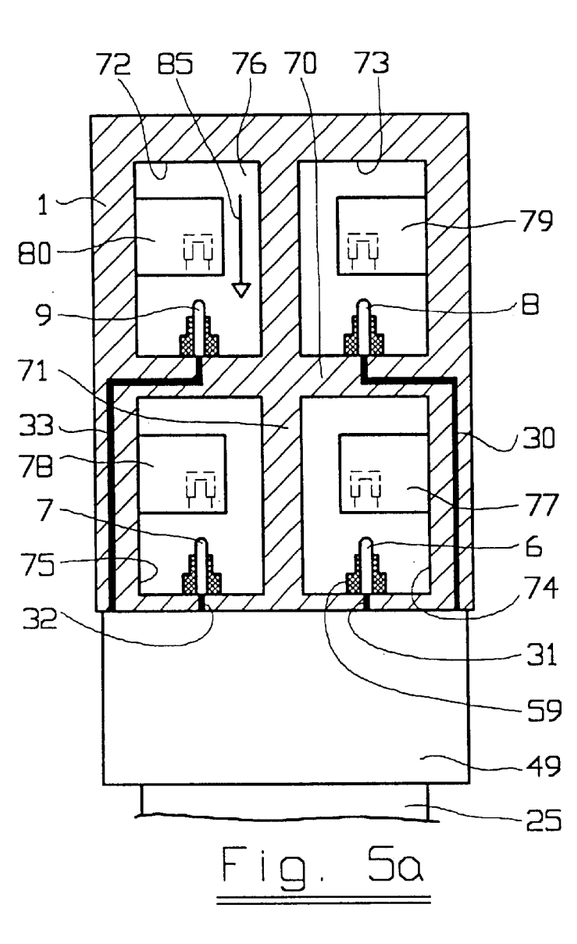
FIG. 5a, 5b, and 5c, an embodiment example with pin contacts that are configured parallel to the level of the holding element.
Figure 5B:
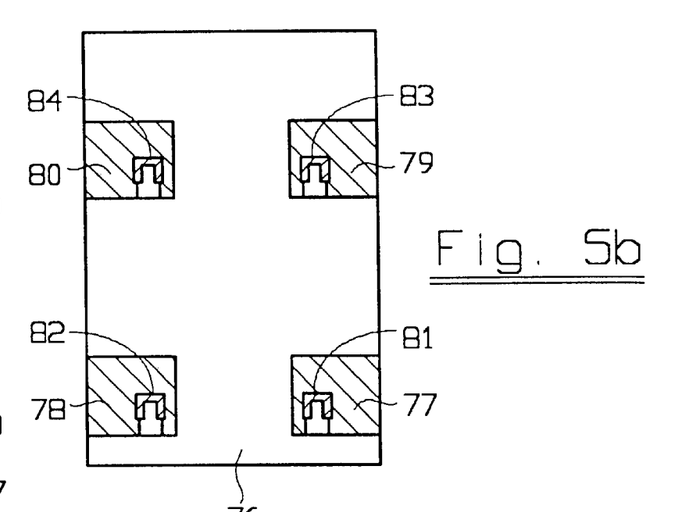
Figure 5C:
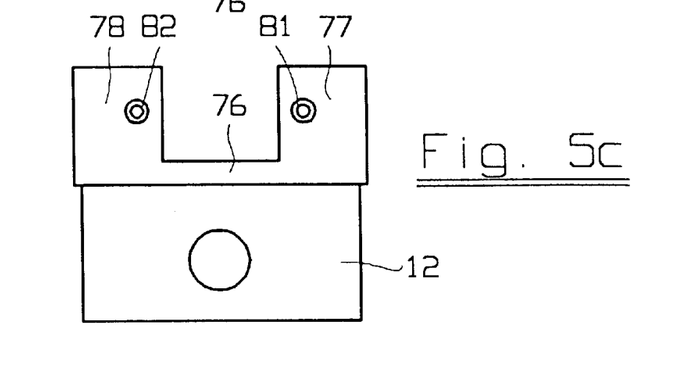

FIGS. 5a, 5b and 5c show another embodiment example of a pressure transducer arrangement in which the holding plate contacts 6, 7, 8 and 9 are also configured as contact pins. This differs from the previous embodiment examples in that the pins are not located on the outer surface but inside the holding element 1. Holding element 1 is configured as a frame featuring symmetrically positioned middle ribs 70 and 71 which produces four rectangular passage openings 72, 73, 74 and 75 into which the holding plate contacts 6, 7, 8, and 9 protrude. The holding plate contacts 6, 7, 8 and 9 are connected by the electronic lines 30, 31, 32 and 33 with connecting part 49 and with the cable 25 connected to it.

Pressure transducer 12 that is schematically illustrated in FIG. 5c is connected to a plate-shaped part 76 from which square-shaped blocks 77, 78, 79 and 80 extend vertically. In blocks 77, 78, 79 and 80, contact sockets 81, 82, 83 and 84 are located that are electrically connected to pressure transducer 12. When the base plate 76 of pressure transducer 12 is attached to holding element 1, blocks 77, 78, 79 and 80 extend into the passage openings 72, 73, 74 and 75 (FIG. 5a). By pushing pressure transducer 12 in the direction of the arrow 85, an electronic connection is established between contact sockets 81, 82, 83 and 84 of pressure transducer 12 and the contact pins 6, 7, 8 and 9 of holding element 1 whereby the elastic sealing elements 59 provided at contact pins 6, 7, 8 and 9 are deformed.

Figure 6:
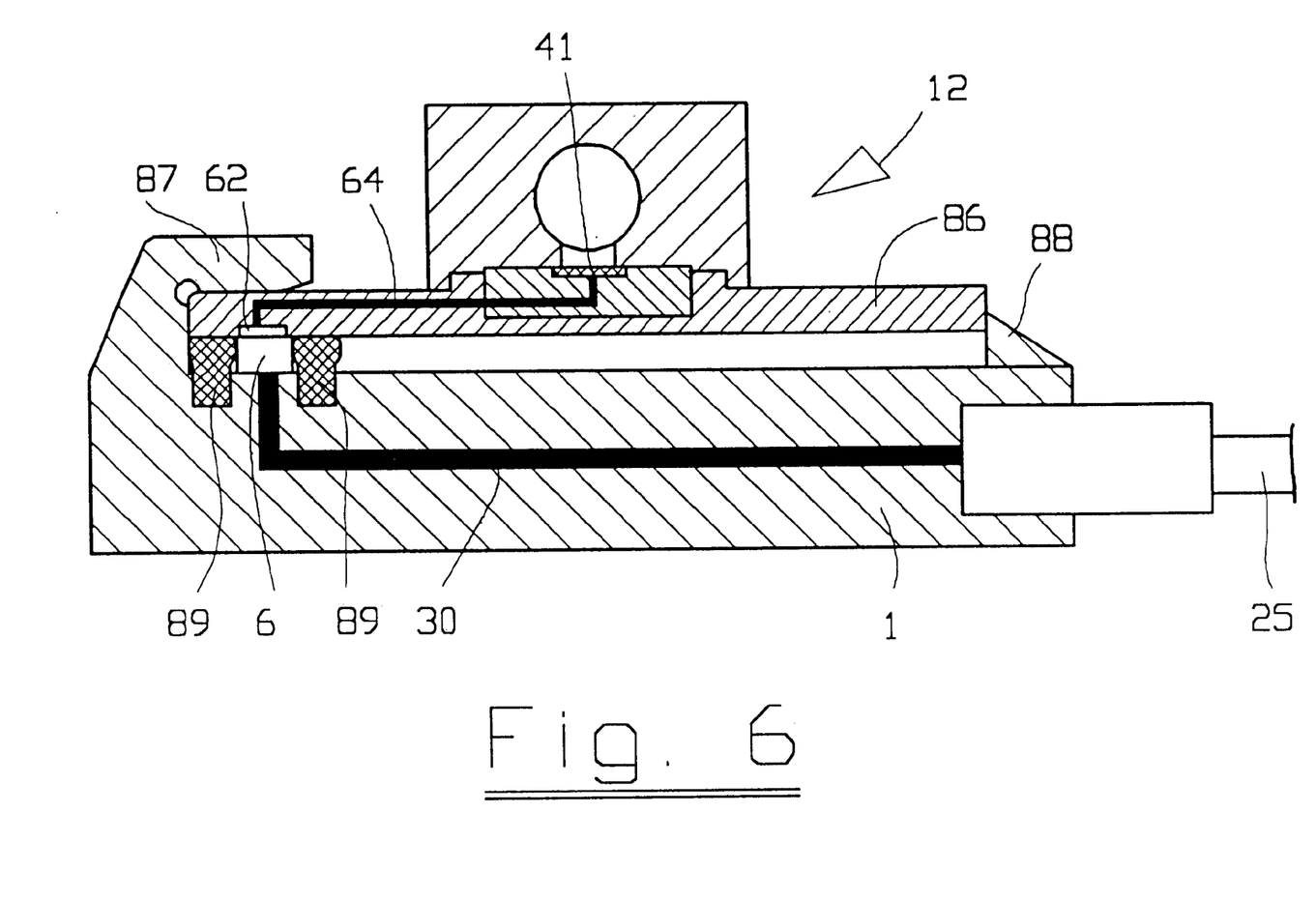
FIG. 6, an embodiment example with touch contacts.

FIG. 6 shows an embodiment example in which the pressure transducer 12 features a plate-shaped element 86 that is engaged between a retaining nose 87 and a catch buckle 88 of holding element 1. Pressure measuring element 41 is connected to the disk-shaped contact 62 through electronic connecting lines, of which here only line 64 is visible. Contact 62 touches counter-contact 6 that is attached on the outside of holding element 1 and electrically connected to cable 25. Counter-contact 6 is enveloped by an elastic sealing element 89 that is attached to holding element 1 and wipes off fluid droplets that may potentially have remained on element 86, thus protecting the contact area against humidity and assisting in attaching pressure transducer 12 as soon as the plate-shaped element 86 of pressure transducer 12 is set against the retaining nose 87.

Figure 7:
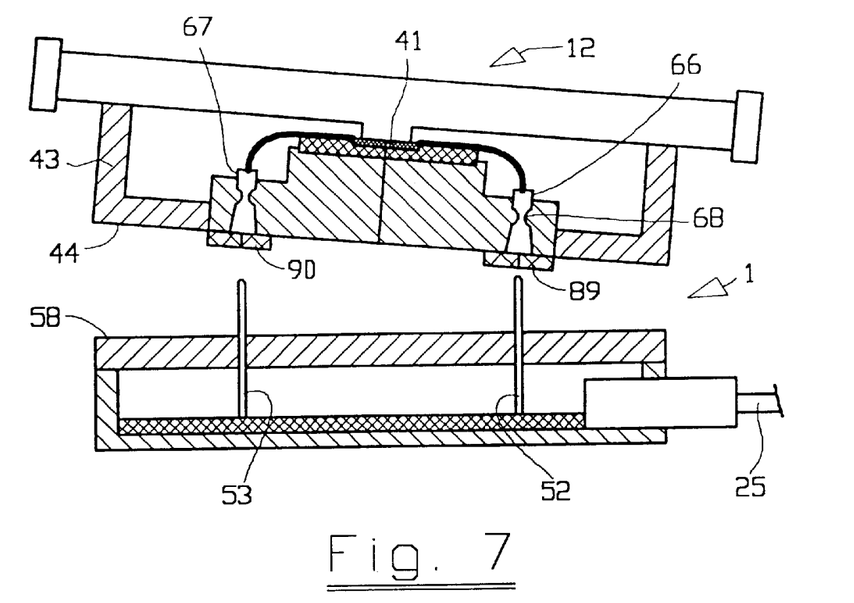
FIG. 7, an embodiment example with fluid-protected pressure transducer contacts.

FIG. 7 shows an embodiment example in which the terminal contacts 66 and 67 that are routed to the external surface 44 of housing 43 of the pressure transducer 41 are covered and protected against humidity by elastic sealing elements 89 and 90. When attaching pressure transducer 12 to the holding element 1 the holding-plate contacts 52 and 53 that are firmly attached to holding element 1 penetrate seals 89 and 90, touch the corresponding contacts 62 and 63, and in this fashion establish an electronic connection between the pressure-measuring element 41 and cable 25.

Figure 8:
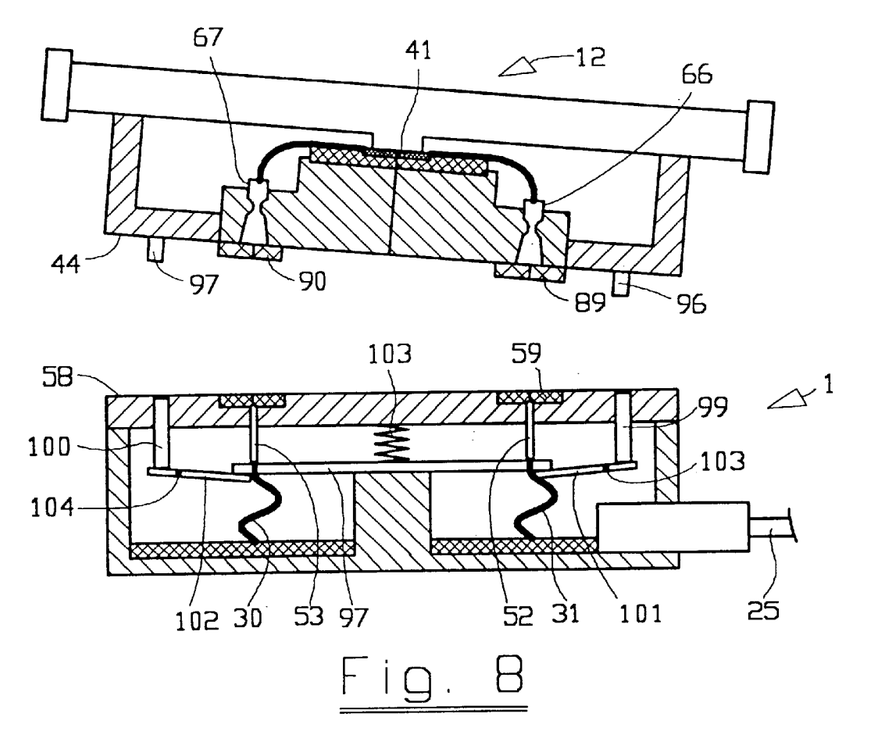
FIG. 8, an embodiment example with retractable holding plate contacts.

FIG. 8 shows an embodiment example with a pressure transducer 12 similar to the one in FIG. 7, whereas at the bottom side 44 of the pressure transducer 12 elevations 96 and 97 are provided. In this configuration, sample-holding-plate contacts 52 and 53 are attached to a plate 97 that is mobile in the longitudinal direction of contacts 52 and 53. An electronic connection between cable 25 and contacts 52 and 53 is established through connecting lines 30 and 31, respectively, which are of sufficient length to facilitate an unimpeded shifting of plate 97.

Alternatively, contacts 52 or 53 can also be electrically connected to cable 25 via corresponding springs according to FIG. 3.

Pressure pins 99 and 100 are provided in holding element 1 exerting pressure upon levers 101 and 102, respectively. The levers 101 and 102 are mounted in holding element 1 in a manner that permits them to pivot around bearings 103 and 104, respectively, that have here only been illustrated schematically. When attaching pressure transducer 12 to the upper surface 58 of holding element 1, elevations 96 and 97 push pressure pins 99 and 100 into holding element 1, which causes levers 101 and 102 to pivot and plate 97 with the attached holding plate contacts 52 and 53 to be pushed into contacts 62 and 63 of pressure transducer 12 against the force of reset spring 103.

Figure 9A:
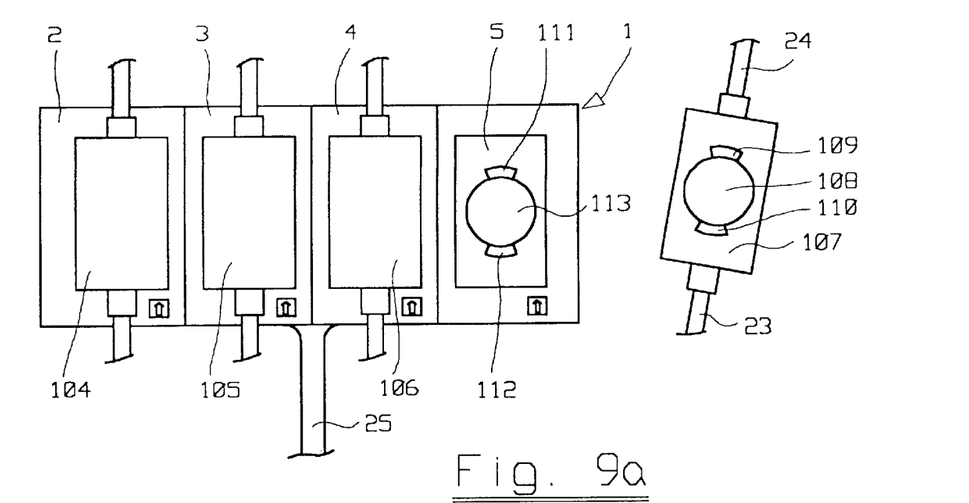
FIG. 9a, an embodiment example with several pressure domes that can be individually attached to the holding element.

FIG. 9a shows an embodiment example in which one-way pressure domes 104–107 are provided that feature an interior cavity which, via hose 23, is pressure-connected to the circulatory system of the patient and connected to the infusion bottle (not shown) via hose 24. On one external surface of the pressure domes 104–107 one elastic pressure transfer membrane 108 is provided for each dome that also are in pressure contact with the cavity. Pressure domes 104–107 show fixture elements 109 and 110, respectively, in the vicinity of the pressure transfer membrane 108 that cooperate together with fixture elements 111 and 112, respectively, that are provided at pressure measuring positions 2–5. Fixture elements 109–112 are here configured as quarter-turn fasteners. To attach pressure dome 104–107, these are set on the pressure measuring positions 2–5 in a "slanted" position and locked into place through a sidewise turn which causes the locking elements 109–112 to lock into each other. Alternatively engagement elements could be provided similar to the engagement elements 10 and 11 in FIG. 1 which would permit the pressure domes to be pushed on the holding element. 1 in a straight line. Stopper 10a clearly defines the final position of the pressure domes.

Each pressure-measuring location 2–5 also features a pressure transfer membrane 113 that, when respectively attached to the pressure domes 104–107, touches the corresponding pressure transfer membrane 108. Pressure membrane 113 that is provided at the individual pressure measuring locations 2–5 is connected to pressure measuring elements (not shown) in pressure connection that are here integrated into the reusable holding element 1. The fluid pressures that are present in pressure domes 104–107 are transferred via the pressure transfer membranes 108 and 113, respectively, to the pressure-measuring elements by means of which they are transformed into electronic signals that can be accessed through the common cable 25.

Figure 9B:
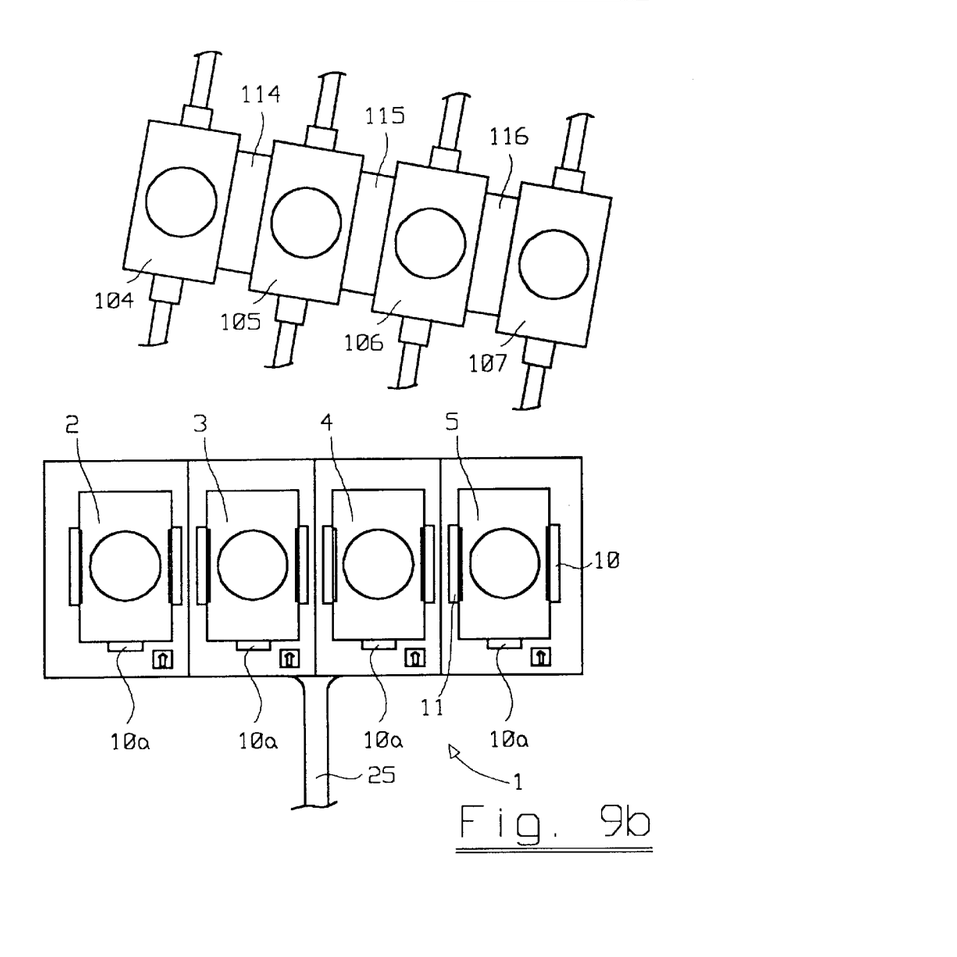
FIG. 9b, an embodiment example with several pressure domes that are positioned alongside each other and can be attached as a unit to the holding element.

FIG. 9b shows an embodiment example with the pressure domes 104–107 interconnected through the connecting elements 114–116 and that can be plugged as a unit into the sockets 2–5 that here—analogously to FIG. 1—feature engagement elements 10 and 11, respectively, for the attachment of the pressure domes 104–107.

Figure 10A:
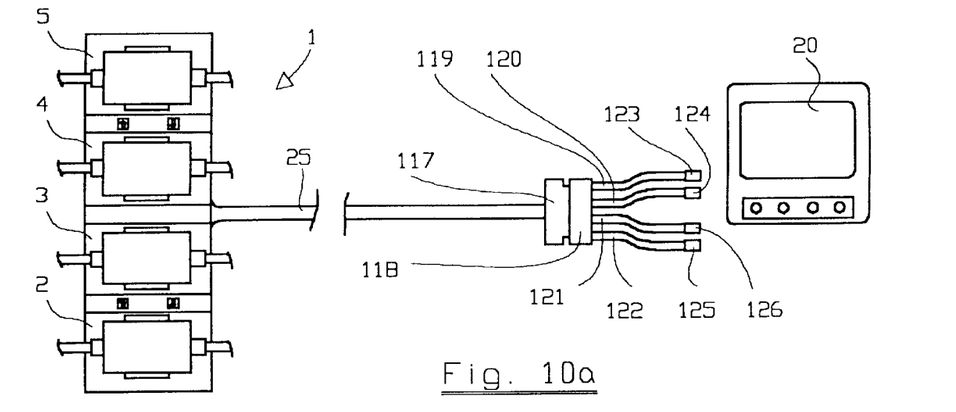
FIG. 10a, an embodiment example similar to FIG. 1 with the cable connected to the monitor via a plug-and-socket connection.

FIG. 10a shows an embodiment example with cable 25 that is attached to pressure-measuring locations 2–5, permanently attached to holding element 1. At the free end of cable 25, a plug-in connector 117 is provided that is plugged into socket 118. Individual monitor cables 119–122 lead away from this socket 118 that are assigned to pressure-measuring locations 2–5 and can be connected to the monitor 20 by means of the corresponding monitor plugs 123–126. Should cable 25 or holding element 1 be damaged, the monitor cables 119–122 and the monitor plugs 123–126 could be re-used.

Figure 10B:
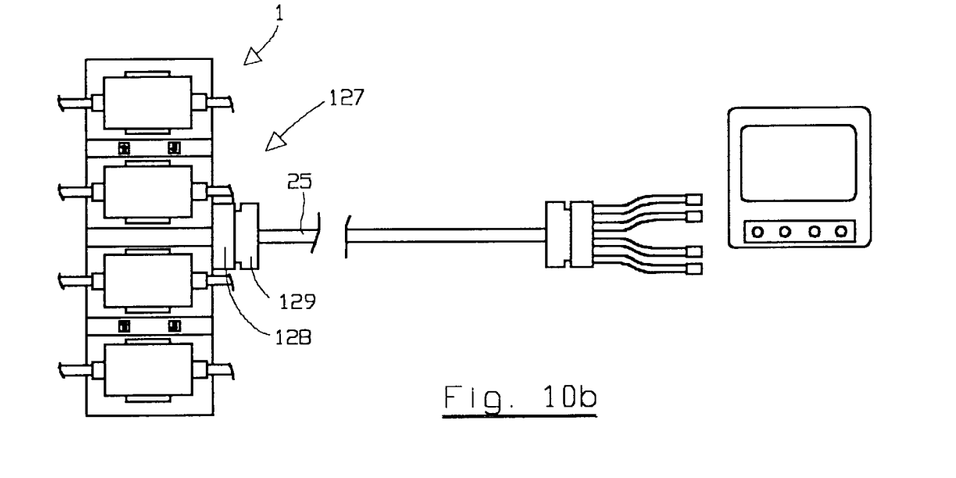
FIG. 10b, an embodiment example similar to FIG. 10a with an additional plug connector for the cable directly on the holding element.

FIG. 10b provides an additional electronic plug-and-socket connection 127, whereas a connecting element 128 is directly attached to the holding element 1 and connected to cable 25 via a connecting element 129. In comparison with FIG. 10a, in this case holding plate 1 and cable 25 can be independently exchanged.

Figure 10C:
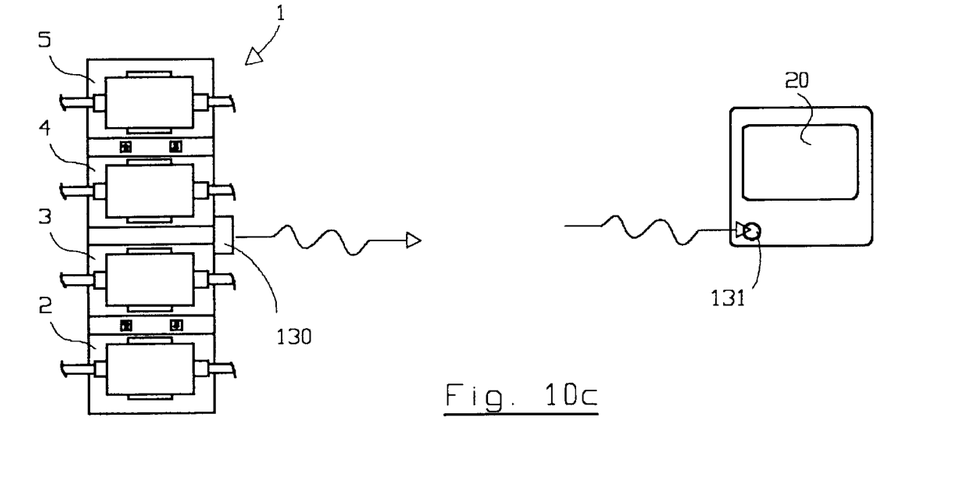
FIG. 10c, an embodiment example with wireless signal transfer.

FIG. 10c shows an embodiment example of a wireless data transmission between the pressure-measuring elements of holding element 1 and the monitor 20. For this purpose, a transmitter 130 is provided on holding element 1 and is connected to the pressure-measuring elements of pressure-measuring locations 2–5 and emits electromagnetic signals that correspond to the measured pressures. These signals are received by a receiving unit 131 of the monitor 20 and displayed.

As various changes could be made in the above embodiments without departing from the scope of the invention, it is intended that all matter contained in the above description shall be interpreted as illustrative and not in a limiting sense.

What is claimed is:

1. A pressure transducer apparatus for invasive blood pressure measurement comprising:
    a holding element adapted for attachment thereto of a plurality of pressure transducers,
    a plurality of counter-contacts on each of said plurality of pressure transducers on the holding element, said counter-contacts corresponding to contacts in electronic connection with a pressure-measurement element, and
    a single common signal transmitter to which are attached all of said counter-contacts for all of said plurality of pressure transducers.

2. The pressure transducer apparatus according to claim 1 wherein said single common signal transmitter is a single holding element cable.

3. The pressure transducer apparatus according to claim 1 wherein said single common signal transmitter is a wireless signal transmitter.

4. The pressure transducer apparatus according to claim 1 wherein the single common signal transmitter is attached to the holding device by means of a detachable electronic plug-and-socket connection.

5. The pressure transducer apparatus according to claim 2 wherein said holding element cable has an end remote from said holding element, which end is connected to a number of pressure transducers by an equal number of connector cables having free ends bearing monitor plugs, and wherein these connector cables are shorter than the holding element cable.

6. The pressure transducer apparatus of claim 1 wherein all of said counter-contacts are located on an external surface of holding element.

7. The pressure transducer apparatus of claim 6 wherein the counter-contacts protrude above the external surface of the holding element.

8. The pressure transducer arrangement according to claim 7 wherein the counter-contacts are contact pins.

9. The pressure transducer apparatus according to claim 1 wherein the holding element comprises a cavity into which the counter-contacts extend, the apparatus further comprising electronic lines inside the holding element which lines are connected to individual insulated conductors of a single common cable, wherein each counter-contact is electrically connected to one of said electronic lines via a spring.

10. The pressure transducer apparatus according to claim 1 wherein the counter-contacts are contact pins arranged on the holding element to be essentially parallel with a level of a surface of said holding element.

11. The pressure transducer apparatus according to claim 10 wherein the holding element is a frame with at least one crosspiece, wherein frame cells are defined by said at least one crosspiece, wherein a first set of said counter-contacts is attached to said at least one crosspiece, wherein a second set of said counter-contacts is attached to the frame, wherein each of said pressure transducers has a plate-shaped element having protruding blocks thereon in which said contacts are located, and which blocks are adapted to be inserted into said frame cells.

12. The pressure transducer apparatus of claim 1 wherein said contacts are terminal contacts.

13. The pressure transducer apparatus of claim 1 wherein said counter-contacts are terminal contacts.

14. The pressure transducer apparatus of claim 1 wherein the holding element comprises elastic sealing elements that partially envelop the counter-contacts in the area of an external surface of holding element.

15. The pressure transducer apparatus of claim 5 wherein a plurality of pressure transducers are firmly attached to each other and are together mounted on the holding element.

16. A pressure transducer apparatus for invasive blood pressure measurement comprising:

a holding element for attachment thereto of a plurality of pressure domes, a plurality of transfer membranes at the holding element with one transfer membrane for each of said plurality of pressure domes, a plurality of pressure transducers with each membrane connected to one of said plurality of pressure transducers, and a single common signal transfer line serving all of said plurality of pressure transducers.

17. The pressure transducer apparatus of claim 16 wherein several pressure domes are combined with each other into one unit and are together attached to said holding element.

* * * * *